US008694267B2

(12) United States Patent
Sunshine et al.

(10) Patent No.: US 8,694,267 B2
(45) Date of Patent: Apr. 8, 2014

(54) AUTONOMOUS MONITORING METHOD AND SYSTEM USING SENSORS OF DIFFERENT SENSITIVITIES

(75) Inventors: Steven A. Sunshine, Pasadena, CA (US); Timothy E. Burch, San Gabriel, CA (US); Gregory Steinthal, Los Angeles, CA (US); Neil Plotkin, Fallston, MD (US); Chang-Meng Hsiung, Irvine, CA (US)

(73) Assignee: Smiths Detection Inc., Edgewood, MD (US)

(*) Notice: Subject to any disclaimer, the term of this patent is extended or adjusted under 35 U.S.C. 154(b) by 0 days.

(21) Appl. No.: 13/610,465

(22) Filed: Sep. 11, 2012

(65) Prior Publication Data

US 2013/0158881 A1    Jun. 20, 2013

Related U.S. Application Data

(60) Continuation of application No. 13/190,123, filed on Jul. 25, 2011, now Pat. No. 8,285,493, which is a continuation of application No. 12/318,425, filed on Dec. 29, 2008, now abandoned, which is a division of application No. 11/111,960, filed on Apr. 22, 2005, now Pat. No. 7,477,994.

(60) Provisional application No. 60/564,233, filed on Apr. 22, 2004.

(51) Int. Cl.
*G06F 19/00* (2011.01)
*G08B 23/00* (2006.01)

(52) U.S. Cl.
USPC ............................................ 702/32; 340/517

(58) Field of Classification Search
USPC ............................................................ 702/32
See application file for complete search history.

(56) References Cited

U.S. PATENT DOCUMENTS

| 4,638,286 A | 1/1987 | Nichols |
| 5,469,369 A | 11/1995 | Rose-pehrsson et al. |
| 5,571,401 A | 11/1996 | Lewis et al. |
| 5,698,089 A | 12/1997 | Lewis et al. |
| 5,801,297 A | 9/1998 | Mifsud et al. |
| 6,085,576 A | 7/2000 | Sunshine et al. |
| 6,234,006 B1 | 5/2001 | Sunshine et al. |
| 6,319,724 B1 | 11/2001 | Lewis et al. |

(Continued)

FOREIGN PATENT DOCUMENTS

JP    2002-357576    12/2002

OTHER PUBLICATIONS

Novak et al., "Nerve agent detection using networks of single-walled carbon nanotubes," Applied Physics Letters, 2003, pp. 4026-4028, vol. 83, No. 19, American Institute of Physics.

(Continued)

*Primary Examiner* — Bryan Bui
(74) *Attorney, Agent, or Firm* — Foley & Lardner LLP

(57) ABSTRACT

A method and system of monitoring for chemical or other toxic agents includes operating a plurality of first type sensors having a first level of sensitivity to an agent in a monitored area. Concurrently a second type sensor is operated having a second level of sensitivity to the agent in the monitored area, where the second level of sensitivity is at least ten times more sensitive than the first level of sensitivity. Input from the plurality of first type sensors and the second type sensor is received and analyzed, at a central location, in order to determine the presence of the agent in the monitored area.

19 Claims, 14 Drawing Sheets

(56) References Cited

U.S. PATENT DOCUMENTS

| | | |
|---|---|---|
| 6,418,783 B2 | 7/2002 | Sunshine et al. |
| 6,422,061 B1 | 7/2002 | Sunshine et al. |
| 6,442,639 B1 | 8/2002 | Mcelhattan et al. |
| 6,537,498 B1 | 3/2003 | Lewis et al. |
| 6,625,569 B2 | 9/2003 | James et al. |
| 6,687,640 B1 | 2/2004 | Gelbard |
| 6,955,787 B1 * | 10/2005 | Hanson ............ 422/50 |
| 7,171,312 B2 | 1/2007 | Steinthal et al. |
| 2002/0141901 A1 | 10/2002 | Lewis et al. |
| 2004/0181346 A1 | 9/2004 | Sunshine et al. |
| 2004/0204915 A1 | 10/2004 | Steinthal et al. |

OTHER PUBLICATIONS

Snow et al., "1/f in single-walled carbon nanotube devices," Applied Physics Letters, 2004, pp. 4172-4174, vol. 85, No. 18, American Institute of Physics.

Pearce, et al., "Chemical Sensor Array Optimization: Geometric and Information Theoretic Approaches," Handbook of Machine Olfaction: Electronic Nose Technology, 2002, Wiley-VCH. pp. 1-32.

Search Report mailed Jul. 13, 2009, received in European Application No. 05856644.9.

Office Action mailed Jul. 7, 2009, received in Japan Application No. 2007-509707.

Notice of Reasons for Rejection mailed Apr. 6, 2010 in corresponding Japan Application No. 2007-509707, with translation.

Office Action in Israeli Appln No. 178789 dated Sep. 16, 2010.

Non-Final Office Action U.S. Appl. No. 13/190,123 dated Oct. 20, 2011.

Notice of Allowance U.S. Appl. No. 13/190,123 dated Jun. 8, 2012.

* cited by examiner

AUTONOMOUS MONITORING METHOD AND SYSTEM USING SENSORS OF DIFFERENT SENSITIVITIES

CROSS-REFERENCE TO RELATED APPLICATIONS

This application is a continuation of U.S. patent application Ser. No. 13/190,123 filed Jul. 25, 2011, which is a continuation of U.S. patent application Ser. No. 12/318,425, filed Dec. 29, 2008, which is a divisional of U.S. patent application Ser. No. 11/111,960, filed Apr. 22, 2005, now U.S. Pat. No. 7,477,994, which claims the benefit of priority under 35 U.S.C. §119(e) to Provisional Application No. 60/564,233, filed on Apr. 22, 2004. The contents of these applications are herein incorporated by reference in their entirety.

FIELD OF THE INVENTION

The present invention relates generally to a method and system for monitoring an area for chemical or other toxic agents using autonomous sensors having different sensitivities.

BACKGROUND OF THE INVENTION

A growing risk of asymmetric attacks has increased the need for distributed chemical detectors or detectors for other agents with vastly superior false positive rates relative to current solutions. Using two tiered sensors for detecting biological or other hazards are known. However, these known arrangement of two tiered sensors typically consist of two types of sensors that are co-located at a sensor location such that the more sensitive or more reliable sensor is only operated or triggered when the less sensitive or less reliable sensor initially detects a presence of an agent that is being monitored.

However, in view of the risks posed by terrorism, some of the chemical warfare and other toxic agents need to be monitored over a vast area. Use of such known co-located dual sensors may be prohibitively expensive if used to cover such a vast area that needs to be monitored.

SUMMARY OF THE INVENTION

In certain embodiments, the present invention provides a method of monitoring for chemical or other toxic agents, including: operating a plurality of first type sensors having a first level of sensitivity to an agent in a monitored area; concurrently operating a second type sensor having a second level of sensitivity to the agent in the monitored area, wherein the second level of sensitivity is at least ten times more sensitive than the first level of sensitivity; and receiving and analyzing, at a central location, input from the plurality of first type sensors and the second type sensor in order to determine the presence of the agent in the monitored area.

In certain embodiments, both the plurality of first type sensors and the second type sensor are operated continuously.

In certain embodiments, both the first type sensors and the second type sensors are chemiresistor based sensor arrays.

In certain embodiments, the chemiresistor based sensor arrays are conductive polymer composite vapor sensors.

In certain embodiments, a preconcentrator is provided with the second type sensor.

In certain embodiments, the present invention provides a system for monitoring for chemical or other toxic agents, including: a plurality of first type sensors, having a first level of sensitivity to an agent, arranged in a monitored area; a second type sensor, having a second level of sensitivity to the agent, arranged in the monitored area, and a central analysis unit connected to the plurality of first type sensors and the second type sensor, wherein the central analysis unit analyzes data from the plurality of first type sensors and the second type sensor in order to determine the presence of the agent in the monitored area.

In certain embodiments, the present invention provides a method for monitoring for chemical or other toxic agents, including: operating a first type sensor having a first level of sensitivity to an agent in a monitored area, operating a second type sensor having a second level of sensitivity to the agent in the monitored area, and receiving and analyzing, at a central location, input from the first type sensor and the second type sensor in order to determine the presence of the agent in the monitored area, wherein the first type sensor and the second type sensor each comprise a plurality of orthogonal sensing technologies on a single sensor array, wherein a transduction mechanism in each of the sensing technologies detects a change in electrical resistance.

In certain embodiments, the present invention provides a system for monitoring for chemical or other toxic agents, including: a first type sensor, having a first level of sensitivity to an agent, arranged in a monitored area; a second type sensor, having a second level of sensitivity to the agent, arranged in the monitored area, and a central analysis unit connected to the first type sensor and the second type sensor, wherein the central analysis unit analyzes data from the first type sensor and the second type sensor in order to determine the presence of the agent in the monitored area, wherein at least one of the first type sensor or the second type sensor comprises a plurality of orthogonal sensing technologies in a single sensor array, wherein a transduction mechanism in each of the sensing technologies detects a change in electrical resistance.

In certain other embodiments, the present invention provides a method of monitoring for chemical or other toxic agents, comprising: operating a plurality of first type sensors having a first level of specificity to a group of agents in a monitored area; concurrently operating a second type sensor having a second level of specificity to the group of agents in the monitored area, wherein the second level of specificity is more specific than the first level of specificity; and receiving and analyzing, at a central location, input from the plurality of first type sensors and the second type sensor in order to determine the presence of the agent in the monitored area.

BRIEF DESCRIPTION OF THE DRAWINGS

The accompanying drawings, which are incorporated in and constitute a part of the specification, illustrate a presently preferred embodiment(s) of the invention, and, together with the general description given above and the detailed description given below, serve to explain the principles of the invention.

DETAILED DESCRIPTION OF THE INVENTION

The applicants have developed low cost, array based, nanocomposite based sensor technology based on earlier work at Caltech as described for example, in U.S. Pat. No. 5,571,401 and its related patents. These patents are incorporated herein for all purposes. This technology has been demonstrated to be sensitive to a wide range of chemicals, environmentally robust, accurate (e.g. not susceptible to false positives), low cost, reliable, and easily upgradeable.

In certain embodiments, the present invention provides a distributed monitoring system based on this technology. This system incorporates highly distributed low cost, less sensitive nodes (or sensors) able to detect at the Immediately Dangerous to Life or Health (IDLH) level and below (as one example of a first level of sensitivity). The system also incorporate "truth nodes" that integrate this detection technology with more sensitive nodes, for example, nodes that include miniaturized pre-concentrators. These "truth nodes" (or more sensitive nodes) detect at a 10 or 100 times lower level of concentration, for example, than the low cost, less sensitive nodes but are often more expensive and take longer to make measurements. The combination of these two detection approaches result in the lowest cost and most highly capable system. This system utilizes the information from the two different node types either individually or collectively at a central location or at a distributed network of locations that are each centrally located for a set of sensors. In certain embodiments, the system also includes a central command monitor that allows all of the nodes in the system to be monitored from one central location. Therefore, for example, each of the distributed network of locations, or a subset thereof, may communicate with the one central location so that the entire system may be monitored from the one central location.

Figure 1:
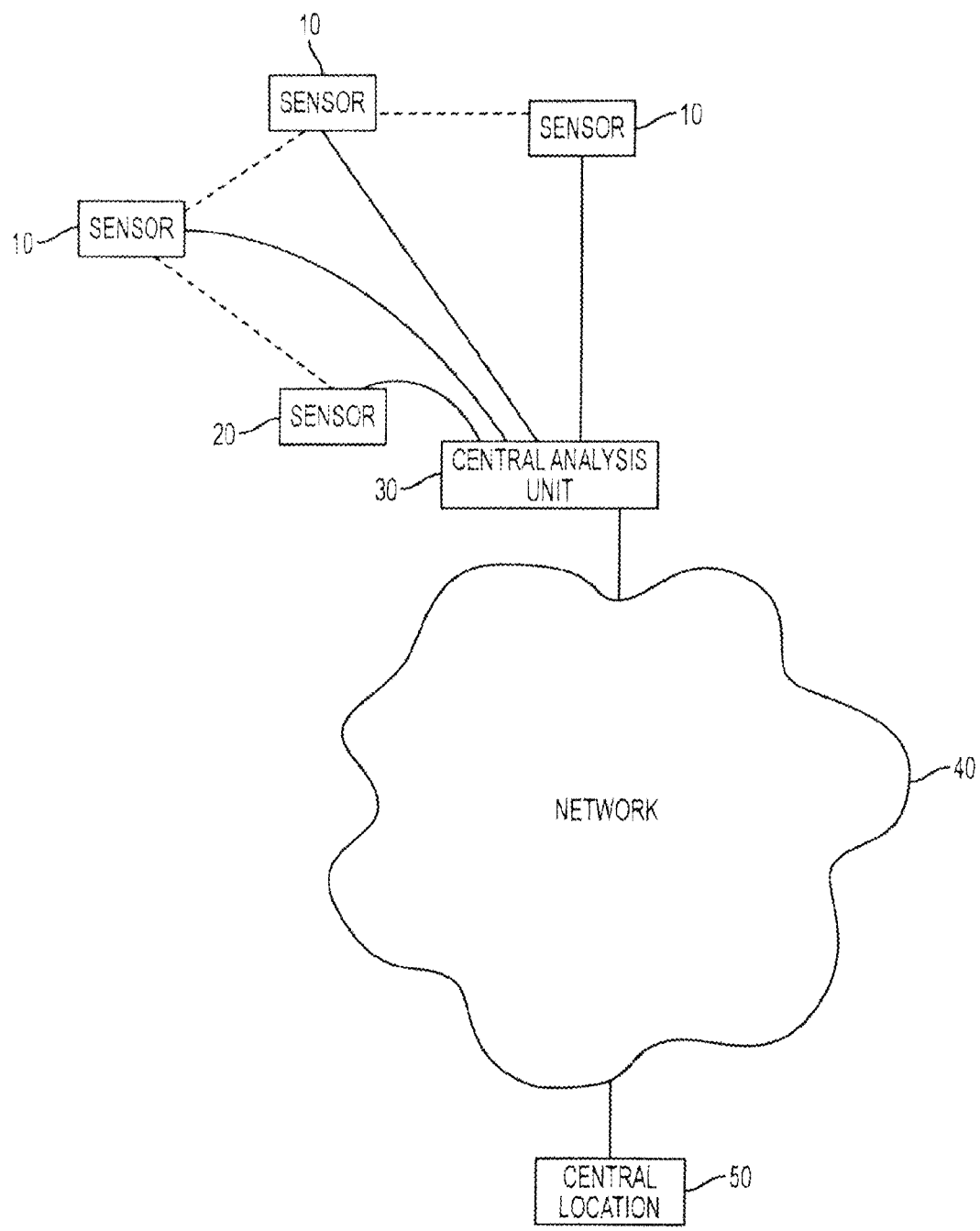
FIG. 1 is a block diagram illustrating the arrangement of sensors in certain embodiments of the present invention.

FIG. 1 is block diagram that illustrates the arrangement of sensors in certain embodiments of the invention. FIG. 1 is exemplary only and one skilled in the art would recognize various modifications and alternatives all of which are considered a part of the present invention. A plurality of first type sensors 10 are arranged to monitor an area and the monitored area also includes one or more second type sensors 20 (only one shown in FIG. 1). Data from the less sensitive or less specific (and therefore typically lower cost and lower power) first type sensors 10 and from the more sensitive (or more specific) second type sensor 20 are sent to a central analysis unit 30. It should be noted that the central analysis unit 30 may be located where it directly receives data from the first type and second type sensor. Alternatively, the central analysis unit may be located at a central location 50 where data from the one or more monitored areas may be transmitted over a public or private wide area network 40 (which may be the Internet which is a public wide area network) to the central location. In yet another alternative, all the sensors in a monitored area may transmit their data to an "intermediate" central analysis unit 30 with a multitude of such intermediate central analysis units transmitting the received data to a remote central analysis unit located at the central location 50. It should be noted that each of the first type sensors 10, the second type sensors 20, the central analysis unit 30, and the central location 50 (with its analysis units) include processors, memory, and program code that are configured to perform the collection, transmission, and analysis of sensor data that is discussed further herein.

The communication from the first type sensor 10 and the second type sensor 20 to the central analysis unit 30 may be by a direct point-to-point communication link as shown by the solid lines in FIG. 1. Alternatively, the first type sensors 10 and the second type sensors 20 may communicate with each other in a mesh type communication network so that the communication originating at one of the sensors reaches the destination central analysis unit 30 through one or more intermediate nodes or sensors. The dotted lines in FIG. 1 are indicative of the communication between the sensors or nodes in such a mesh communication network which enables an originating sensor or node 10 or 20 to communicate with the central analysis unit 30.

The first and second type sensors provide a low cost, low power and highly sensitive chemical detector capable of continuous distributed monitoring of both chemical warfare agents (CWAs) and toxic industrial chemicals (TICs) and provides for improved monitoring of buildings and facilities.

As discussed earlier, applicant has developed low cost, array based, nanocomposite based sensor technology based on earlier work at Caltech. This technology has been demonstrated to be sensitive (IDLH and PEL detection) to a wide range of chemicals, environmentally robust, accurate (e.g. not susceptible to false positives), low cost, reliable, and easily upgradeable. This core technology is reviewed below and results supporting the performance standards are detailed.

One embodiment of the present invention proposes a distributed monitoring system based on this technology. This system incorporates highly distributed low cost nodes (or first type sensors) able to detect at the Immediate Danger to Life or Health (IDLH) level of concentration and below. The system will also incorporate "truth nodes" (or second type sensors) that are more sensitive and detect much lower concentrations of the agents of interest. For example, these truth nodes may integrate this detection technology with miniaturized preconcentrators. These "truth nodes" may detect at 10 to 100 times lower level than the low cost nodes but are typically more expensive and take longer to make measurements. The combination of these two detection approaches result in the lowest cost and most highly capable system possible.

Most simple, low cost chemical sensors produced today are directed at the detection of a single compound or class of compounds. Typical examples include electrochemical cells, metal oxide semiconductors (so called Taguchi sensors), pilasters, and photionization detectors. More sophisticated systems designed to identify multiple chemicals are complicated but vacuum systems, complex sampling systems, or expensive detection schemes. Recently, array based sensors have been demonstrated that combine the ability to identify a wide range of analytes with the low cost and simplicity of single compound detectors.

Figure 2:
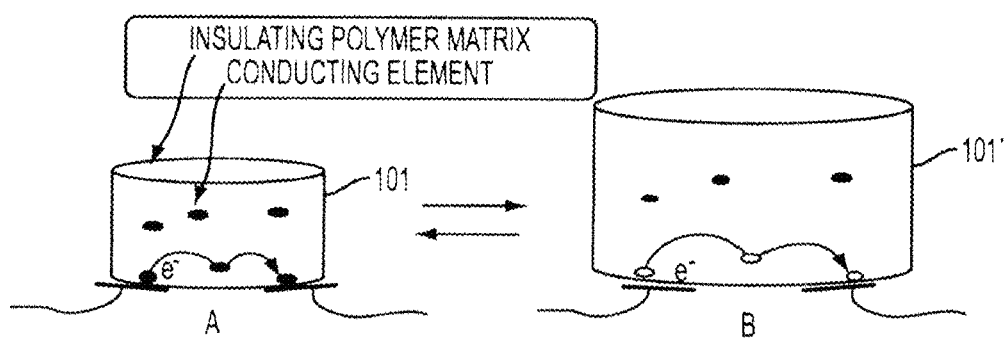
FIG. 2 illustrates the change in property of a polymer in the presence of a vapor.

Arrays of conductive polymer composite vapor sensors were developed at Caltech and have been optimized by applicant. In this approach, the presence of a chemical is detected through a change in the electrical resistance of a chemically sensitive resistor. These sensor films are derived from composites that contain regions of a conducting phase with regions of an insulating organic material. This approach allows use of a wide range of polymeric materials with a range of chemical binding properties, so that an enormous diversity in array composition can be achieved using readily available conventional polymeric materials. When a vapor is present, sorption-induced swelling of the polymer produces a change in the electrical resistance of the material due to the swelling of the film. As shown in FIG. 2, when the vapor is removed, the swelling reverses (see 101 and 101') and the resistance returns to its original value. These responses of these sensors have been proven to be are reversible over tens of thousands of vapor exposures as well as reproducible over a large number of trials under a variety of ambient conditions. With the emergence of newer nanomaterials that can serve as the conducting phase, even greater chemical diversity and sensitivity is achievable.

Figure 3:
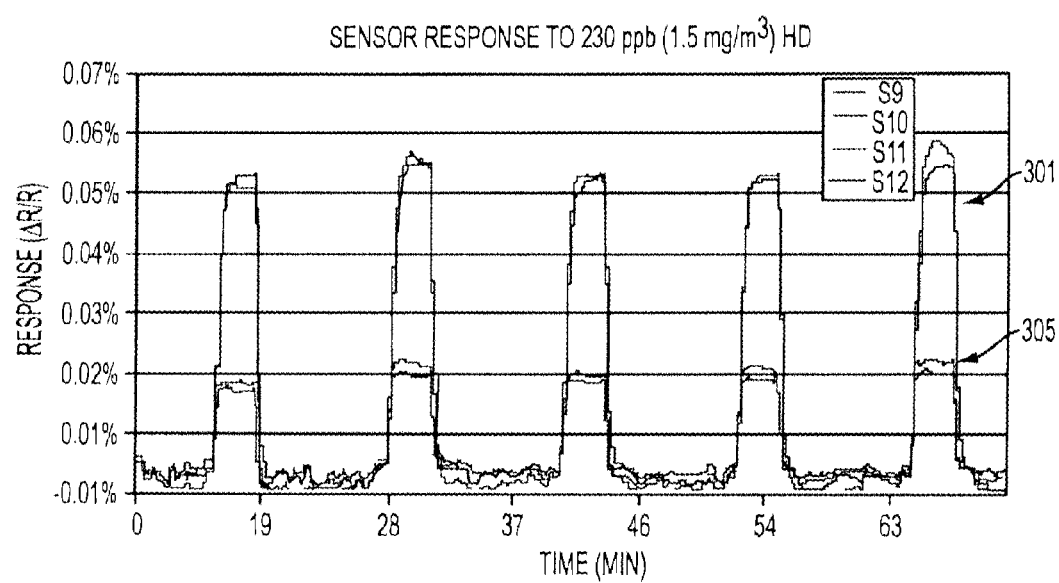
FIGS. 3 and 4 provide examples of the data obtained for testing of sensors with HD and GA.
Figure 4:
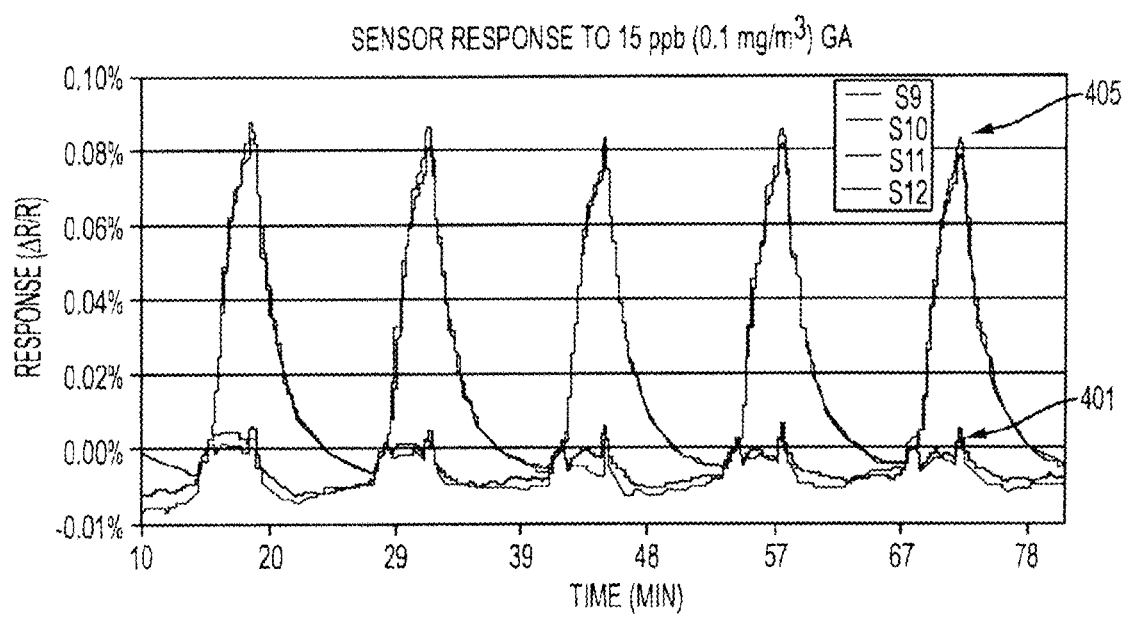
Figure 5:
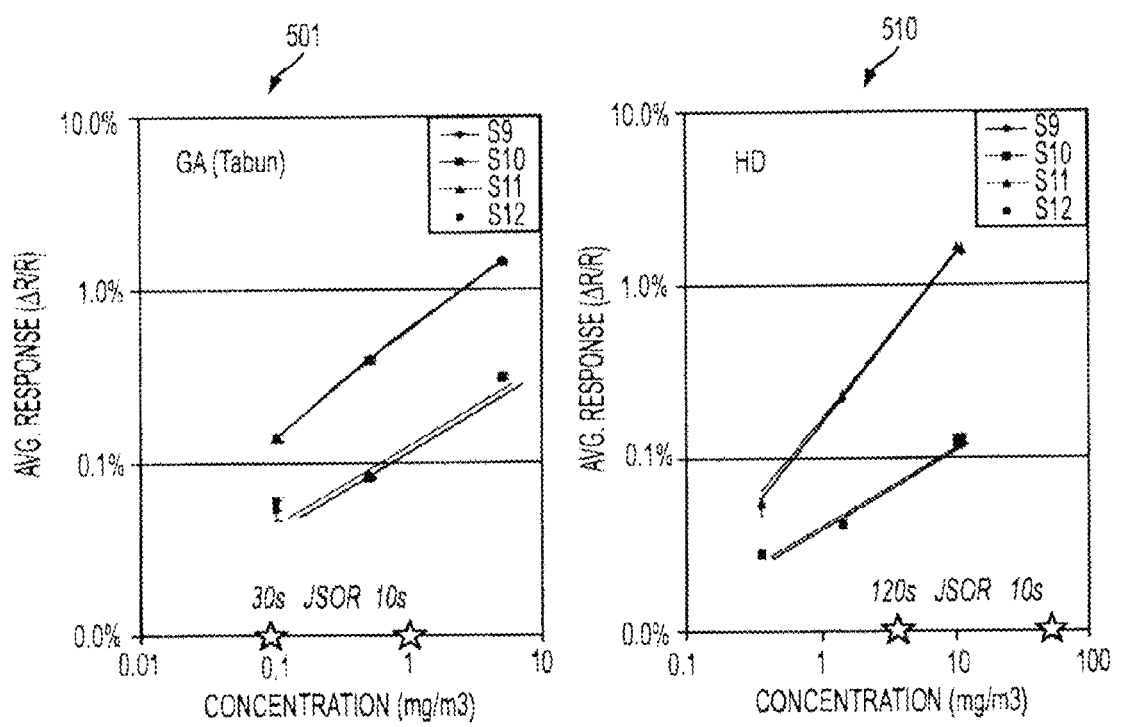
FIG. 5 is a diagram illustrating a tested sensor's response over a range of blister (0-5 mg/m$^3$) and nerve agent (0-1 mg/m$^3$) concentrations.

To verify the sensitivity of these sensors, live agent testing at Battelle Memorial Institute (BMI) has been completed. Test results for HD, GB, GA, DMMP and phosgene (CG) in air confirm detection of low parts per billion level of agents for a hand held chemical point detector. In addition, a high degree of response repeatability and sensor stability was demonstrated even at the lowest limit of detection. An example of the data obtained for HD and GA is shown in FIGS. 3 and 4. For these sensors, discrimination between HD and GA is seen clearly between sensors 9 and 11 and sensors 10 and 12 at all concentrations tested. As shown in FIG. 3, the results 301 for the sensors for blister agent detection is much superior to the results 305 for the nerve agent sensors in the presence of HD (a blister agent). Likewise, as shown in FIG. 4, the results 405 of the nerve agent sensors is much superior to the results of the blister agent sensors in the presence of GA (a nerve agent). In general, as shown in FIG. 5, these tested sensor's display a linear response (see 501 and 510 in FIG. 5) over a wide range of blister (0-10 mg/m$^3$) and nerve agent (0-100 mg/m$^3$) concentrations.

Figure 6:
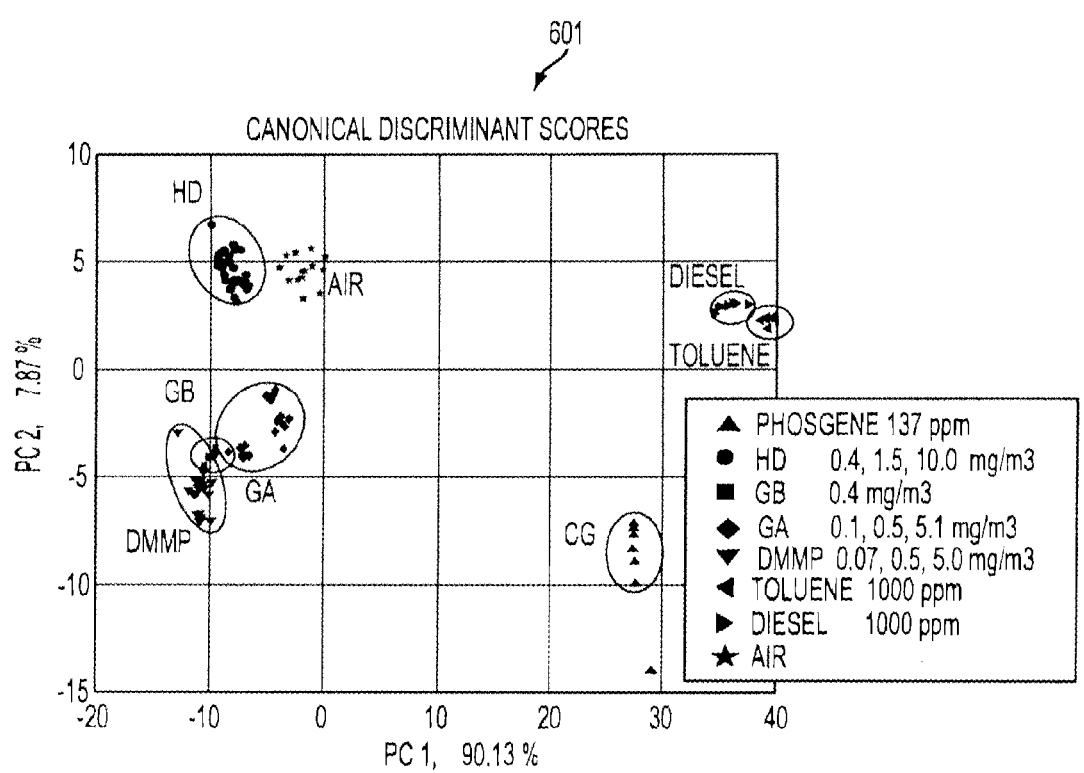
FIG. 6 is a discrimination plot for chemical warfare agents over wide ranges in concentration.

In addition to H and G-series agents, these composite sensors also show remarkable sensitivity to higher vapor pressure (>1 atm) blood and choking agents, phosgene (CG) and hydrogen cyanide (AC). An example of the response measured for 137 ppm phosgene is shown in the discrimination plots 601 in FIG. 6 where even at this low concentration, the new sensor array can clearly distinguish between all the agents tested, as well as common chemical interferents (toluene, diesel fuel). It is estimated that the detection levels for detection of blood or choking agents are in the low ppm range.

In certain embodiments, the sensitivities described above can be further enhanced by incorporation of a miniaturized preconcentrator. Prior work has clearly indicated that sensitivities of 100 fold are achievable with miniaturized preconcentrators. This allows for Permissible Exposire Limit (PEL) level detection even in instances where the fundamental sensing technology cannot achieve this level. Therefore, certain embodiments of the present invention provide for combining simple sensing nodes for IDLH (or less sensitive) detection with more sophisticated nodes that incorporate preconcentrators for PEL (or more sensitive) level detection.

Figure 7:
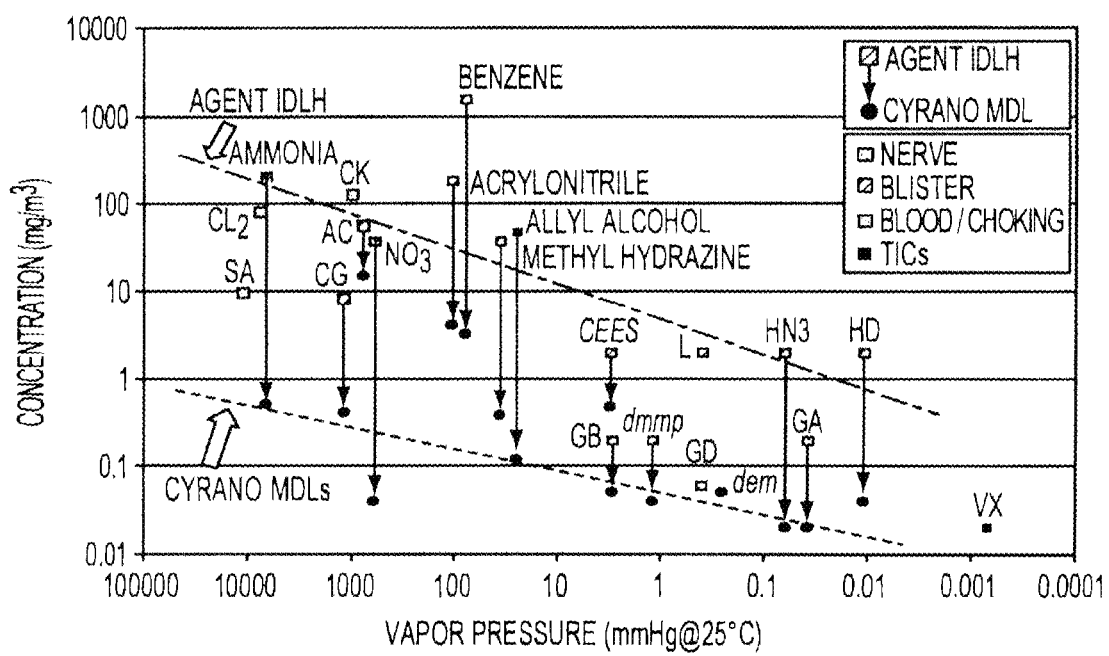
FIG. 7 is a diagram that illustrates the detection limit of sensors to a wide range of analytes.

As shown in the diagram 701 of FIG. 7, the detection limit of these sensors to a wide range of analytes has been measured and is commonly in the low ppb for CWAs and TICs. While the absolute detection levels of gases such as hydrogen cyanide and phosgene are higher than those for CWAs, the detection capability is still significantly below immediately dangerous to life and health (IDLH) levels.

Figure 8:
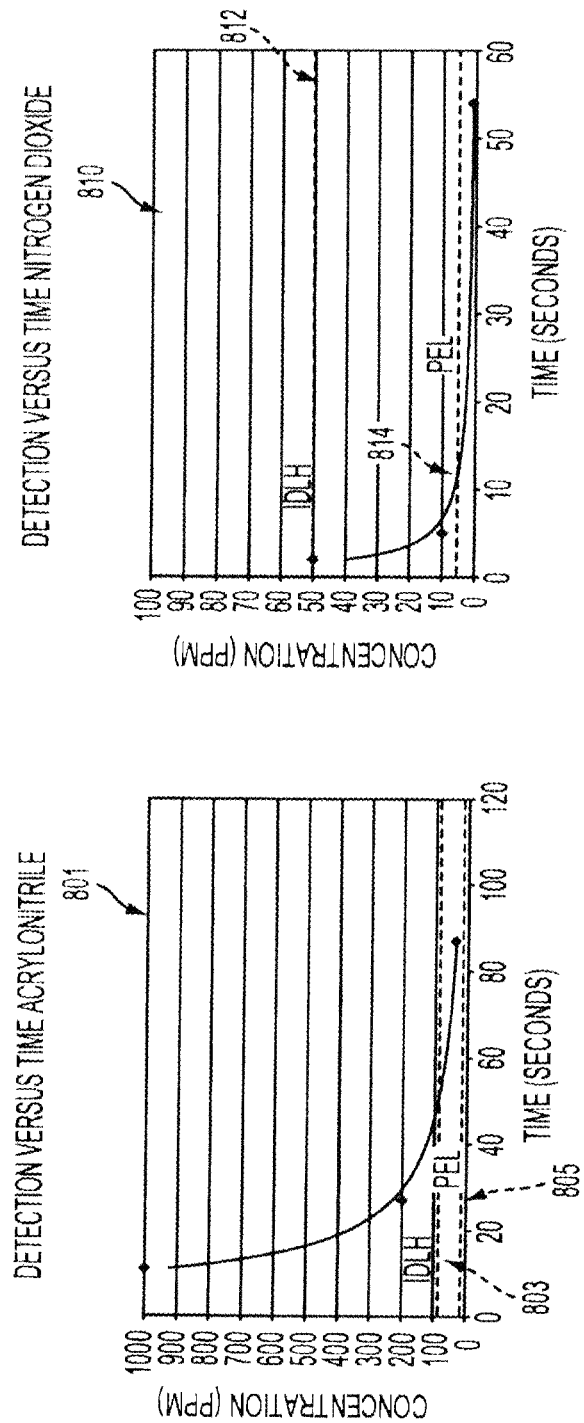
FIG. 8 is a graphical display of the time to detect versus concentration for specific toxic industrial chemicals.

Results for specific TICs (NO$_2$ 801 and acrylonitrile 810) are presented in FIG. 8 in the form of time to detect versus concentration curve. Applicant has already developed sensor materials that can detect TICs of interest at or below IDLH (803, 812) and PEL (805, 814) levels in well less than two minutes and further improvements are achievable.

Any sensing system must be able to perform under a wide range of external conditions including wide variation in humidity, temperature, and confounding environments. The live agent testing has included testing sensors over a varying temperature and humidity.

Detection on fully autonomous devices was determined as part of a validation study on five hand held devices with temperature varied between 10 and 40° C., humidity between 1-80% relative humidity, and interfering elements including 1% each of AIFF, diesel fuel, bleach, antifreeze, ammonia, vinegar, floor wax, Windex, and Spray 9 cleaner. These results are summarized below. The results indicated that the devices were able to detect G series nerve agents at or below the Joint Services Operational Requirement (JSOR) requirements (0.1-1.0 mg/m$^3$) and was able to detect blister agents below JSOR requirements (2 mg/m$^3$).

With respect to temperature, the following results were observed:

At 0° C., all 5 tested units were operational (function test only, no agent challenge).

At 10° C., all 5 tested units correctly alarmed to GB and HD in all tests (10/10).

At 40° C., all 5 tested units correctly alarmed to GB and HD in all tests (10/10).

Based on the above results, temperature and humidity are not significant risks to reliable operation of the sensors used in certain embodiments of the present invention.

In total, over 300 validation experiments were conducted on 5 different hand held devices. Overall prediction success for one of these units has been analyzed using receiver operator characteristic (ROC) curves. The results of these experiments clearly demonstrated very favorable specificity (false positive ratio) and sensitivity (false negative ratio).

One of the advantages of sensors provided by the present invention is that it uses technology characterized by the low cost nature of the sensing materials as well as the read out electronics and the use of such sensors in the two or more tier arrangement discussed herein wherein a plurality of low cost sensors (of lower sensitivity and/or specificity) are arranged concurrently with a higher cost sensors (of higher sensitivity and/or specificity) so that a large area can be continuously and effectively monitored for chemical and other toxic agents. This arrangement of low cost sensors is ideally suited for a widely distributed, low cost monitoring system.

This sensing technology has been tested in the industrial market and this product has demonstrated excellent reliability in the field. In addition to this field experience, extensive laboratory testing of the sensor technology itself has been conducted. These tests indicated little sensor degradation, even when challenged with higher than expected agent concentrations.

Another element of a successful sensor is that the manufacturing process be robust with high manufacturing yields. Applicant has developed a robust manufacturing process for polymer composite sensors. The sensor uniformity was recently investigated for the arrays sent for live agent testing. A comparison of the training data for six units under test demonstrated a high degree of uniformity across these units.

Another feature of certain embodiments of the present invention is the expandability of the system. Because the detectors use an array based approach and these sensors are broadly sensitive to a wide range of chemistry, the system can easily be upgraded to detect new threats by updating the identification algorithms, either on board the device, or through a centralized data analysis system. In fact, the commercial hand held device that is sold by applicant is designed to be "user trained" so that the same product is used in a vast array of different applications by simple changes to the on-board algorithms. The instrument is designed so that these changes can be made by the end user. In one embodiment, these upgrades are provided to the user via downloadable software upgrades (if local data analysis is implemented) or in a seamless manner if remote data analysis is implemented.

Figure 9:
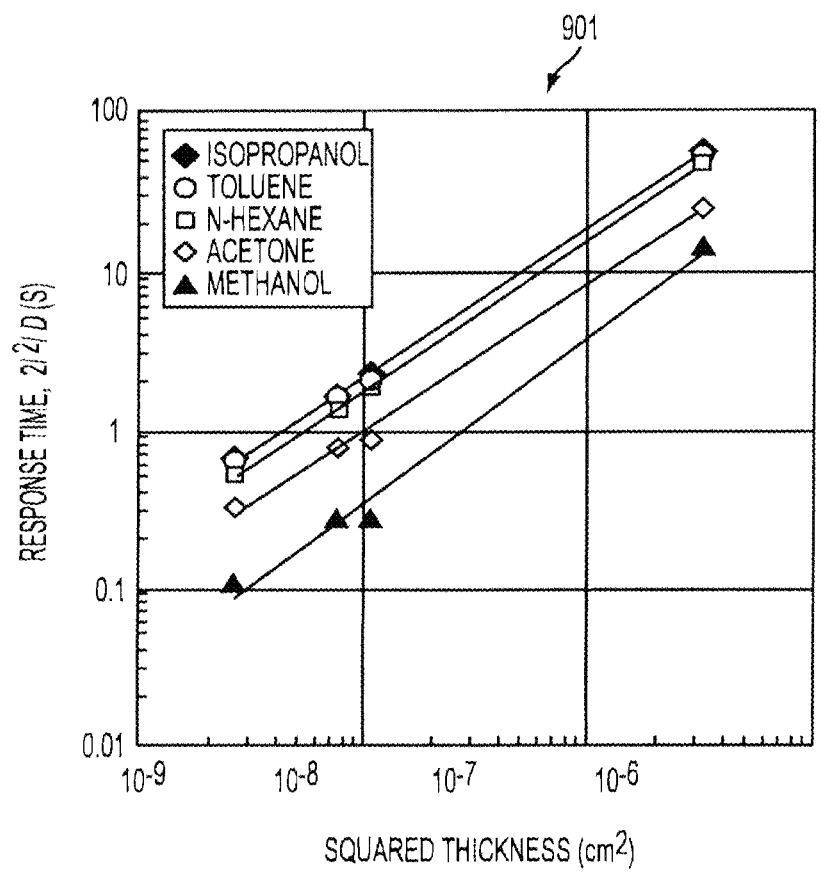
FIG. 9 is graph illustrating sensor response times versus film thickness for polymer composite sensors.

As discussed earlier herein, certain embodiments of the present invention use polymer composite sensors for CWA and TIC detection. The performance of these existing materials can be improved through improved deposition methods and control of film thickness. As shown in the graph 901 in FIG. 9, while the response of these sensors is rapid (typically less than 30 seconds), the response time is proportional to $t^2$, where t is the film thickness. Thus, a reduction of film thickness from 1 micron (for example, the film thickness in certain embodiments) to 500 nm improves response time by 4 fold and result in response times significantly less than ten seconds. Thus, certain embodiments of the present invention provides for an improved sensor with a film thicknesses less than or equal to 500 nm and ideally with a film thicknesses less than 100 nm.

Additional improvements in the composite sensors can be accomplished through modifying both the non-conducting and conducting phases as a part of investigating materials and optimizing their performance. There are indications that some of these materials may have sensitivities that are 4-10 times better than previously demonstrated.

In certain embodiments, the present invention uses novel filler materials that improve sensor sensitivity. Recent work with single wall carbon nanotubes (SWNTs) has demonstrated a potential for enhanced sensitivity to a wide range of chemicals including nitrogen dioxide and other strong oxidizing or reducing agents. It has also been recently demonstrated that certain metal nanoparticle conductors also produce sensors with enhanced chemical sensitivity and these sensors are also used with certain embodiments of the present invention. Use of SWNTs and SWNT networks is described, for example, in J. P. Novak et al., APPL. PHYS. LETT., vol. 18, 4026 (2003), which is incorporated herein for all purposes.

In addition to enhanced sensitivity, it is imperative that any new materials are also robust to changing environmental conditions. For each sensor material described above, comprehensive testing of sensitivity, response to humidity, temperature stability, and sensitivity to interference compounds is performed to test the robustness of the sensor materials to environmental conditions.

Figure 10:
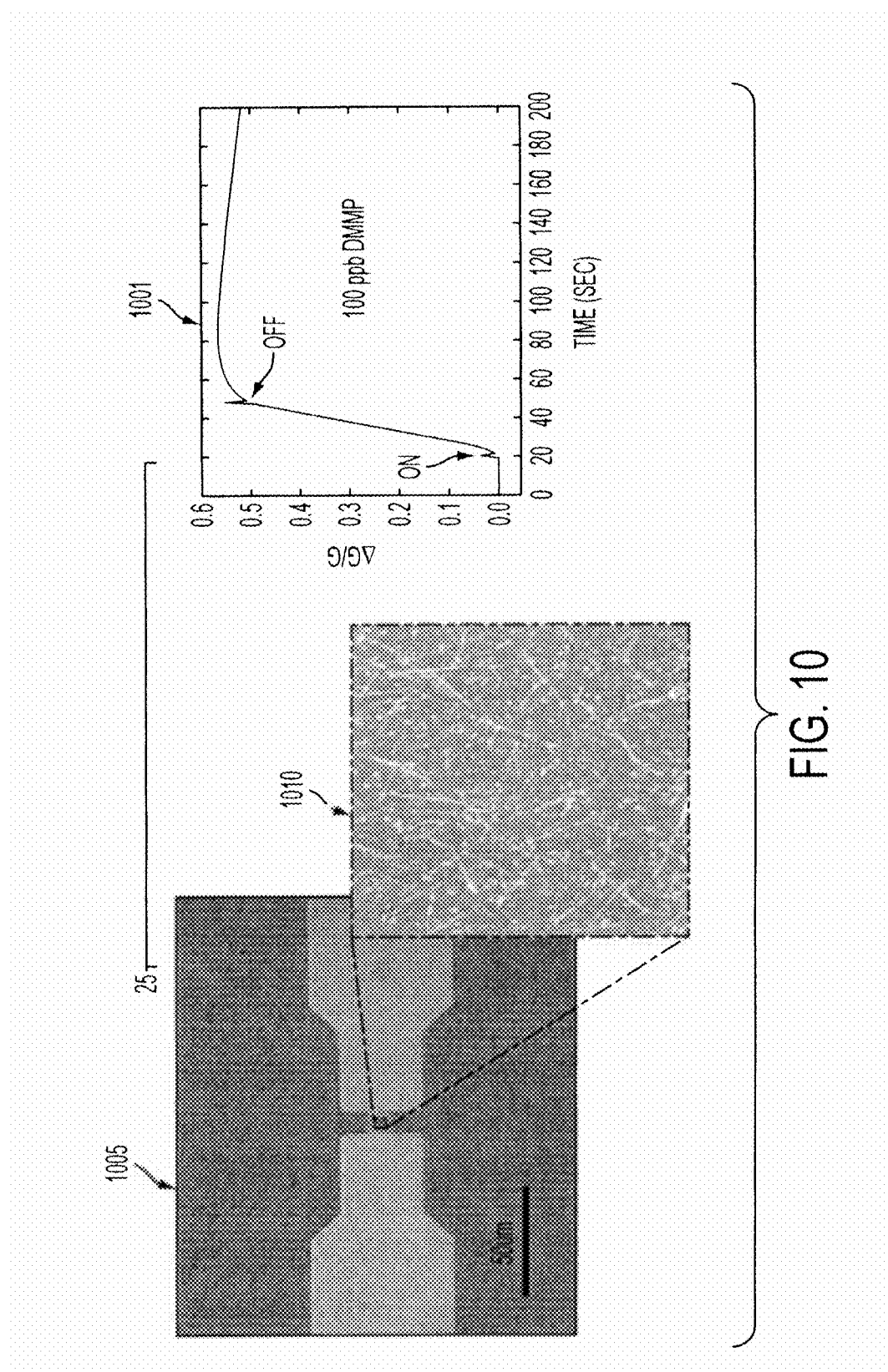
FIG. 10 is diagram illustrating the use of a SWCNT network chemiresistor as a sensor.

Initial results focused on CW simulant detection clearly indicate that these sensors are sensitive to DMMP, a standard nerve agent stimulant, as shown in the graph 1001 in FIG. 10. FIG. 10 also shows an optical image 1005 and an AFM image 1010 of a SWNT network chemiresistor and the measured change in resistance upon exposure to 100 ppb if a chemical simulant for nerve agents. The SWNT networks can be patterned with high yield using conventional photolithographic techniques. The use of SWNT networks eliminates the need to position individual SWNTs and produces a more easily manufacturable device with a more reproducible response.

To monitor sensor performance, extensive laboratory testing is conducted on the sensor materials. Detection versus response time curves are generated and an initial determination of $P_{fp}$ (probability of false positives) and $P_{fn}$ (probability of false negatives) are conducted. Some of these arrays are then sent out for live agent testing (at a mutually determined surety laboratory) and others are incorporated into the initial prototypes for system testing. In certain embodiments, the system parameters including the analytical models are adjusted so that a target $P_{fa}<0.1\%$ and a target $P_{fn}<5\%$ is achieved for all compounds tested at the IDLH level of concentration without preconcentration.

The optimal sensor array uses orthogonal sensing technologies on a single, simple, platform. Thus, the optimal sensor array includes several different chemiresistor approaches, possibly including sensors in a single sensor array made from regions of conducting and non-conducting materials, sensors based on intrinsically conducting polymers (ICPs) and composites made from ICPs, sensors made from single wall carbon nanotubes (SWNTs) and composites made from SWNTs, metal oxide semiconductor sensors, sensors based on porphyrin materials, and sensors based on metallic nanotubes made from metals and metal oxides. In general, in certain embodiments which use orthogonal sensing technologies, each sensor array includes different types of sensors in which the transduction mechanism in all sensors measure a change in electrical properties. Furthermore, in certain embodiments, the at least one of the sensors has regions of conducting and non conducting material.

Figure 11:
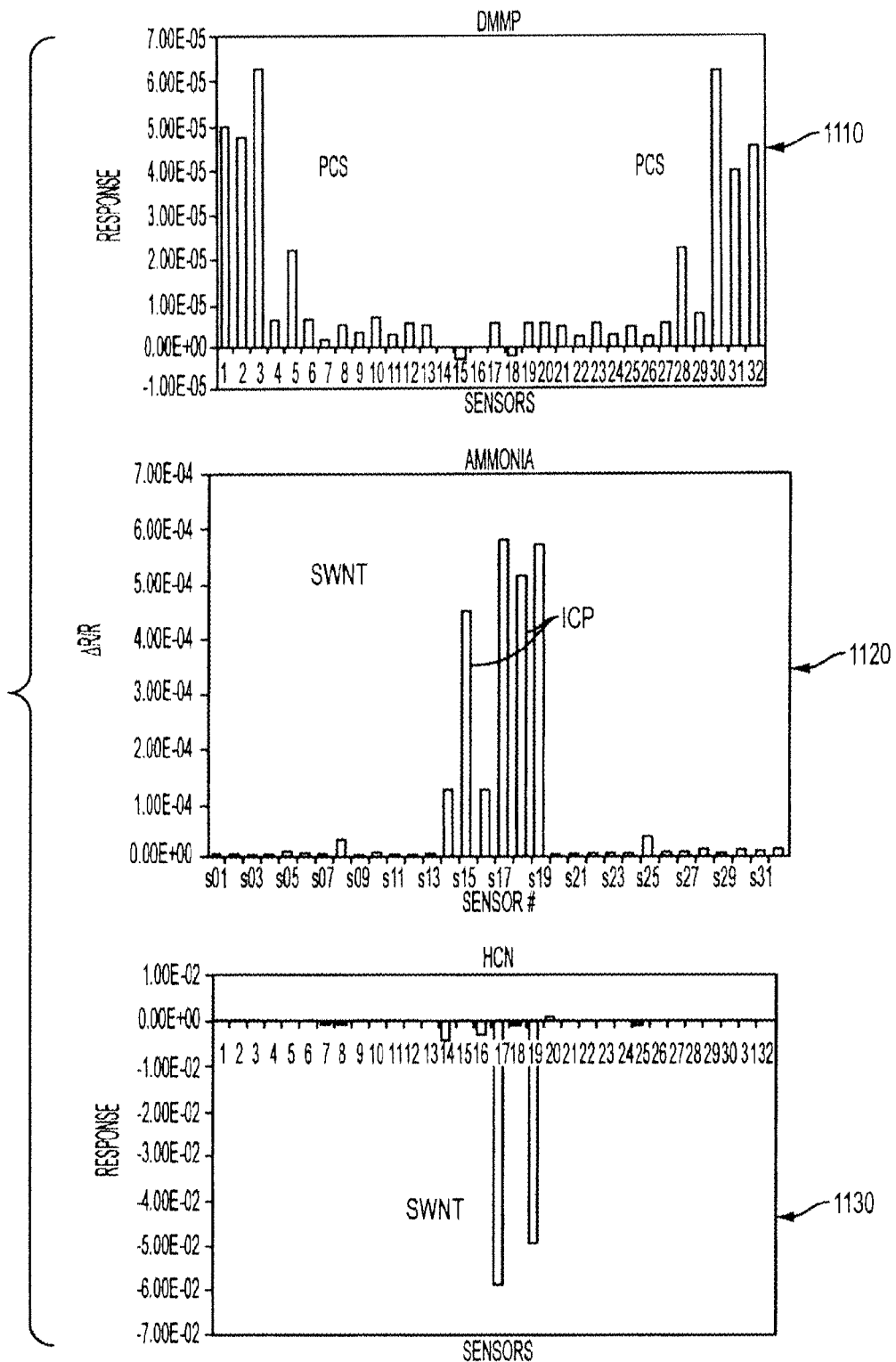
FIG. 11 is a diagram that illustrates performance of a sensor array consisting of different types of chemiresistors to different analyte vapors.

FIG. 11 is a diagram that illustrates performance of a single sensor array consisting of different types of chemiresistors. As illustrated in FIG. 11, such an array made from multiple types of thin film chemiresistors sensors exhibits a highly differentiated pattern of response to different classes of analyte vapors. Graph 1110 displays the response of the PCS polymer composite sensors in the single sensor array to DMMP in the air at IDLH concentration level, graph 1120 displays the response of SWCNT and ICP conducting polymer sensors in the single sensor array to presence of ammonia in the air at IDLH concentration level and graph 1130 displays the response of the SWCNT sensors in the single sensor array to the presence of HCN in the air at IDLH concentration level. The use of orthogonal sensing technologies in a single sensor array provides for greater reliability and range of detection by the sensor array.

One of the features of certain embodiments of the present invention is provision of an electronic platform that provides low noise measurements, and appropriate power and communications interfaces. While the detailed design of these components may be refined, a current design is described in more detail in the following paragraphs.

Applicants have determined that current performance is limited by electronic noise rather than sensor noise. Therefore, there is a focus on improving the electronics design to improve overall signal to noise, and therefore sensitivity, by decreasing the electronic noise. An electronic noise reduction of 10× could lead to a 10 fold sensitivity enhancement.

One of the issues in certain embodiments of present invention concerns how to communicate alarms back to a centralized location. There are two competing techniques that may make sense depending on installation issues (time, installation cost, etc). One approach is using a power line carrier. This approach provides a reliability benefit since a wire is used to communicate key information and a cost benefit as it uses pre-existing infrastructure to carry this information. The restriction to this technique is that the sensor must be connected to a power line which can add installation cost and/or restrict available deployment locations.

The second approach would be a wireless communication protocol. With improved mesh networks this approach offers the advantage of being able to locate a device anywhere (assuming adequate battery power) and reduced installation costs. However, this approach may result in a less reliable connection in an application where data flow is critical.

The system of this invention is designed to use, among others, wireless or power line carrier communications and to include a modular approach so that the communications module is a separate part of the sensor node. This allows for a common sensing platform that could be utilized with different communications methods.

With respect to power, the sensor devices can be either battery or line powered with battery back-up. The advantage of line power is a lower cost of ownership, ability to move away from ultra low power designs, and greater design flexibility of power hungry elements such as the preconcentrator. The advantage of using battery power is the freedom of placement and lower cost of installation (if new power connections are required).

In certain embodiments, the system may be designed for distributed monitoring throughout a building or other location. Therefore, the information collected at each sensor can be best utilized if it is brought back to a central location. Once centralized, this data can be fused and further interpretation can be conducted. In addition, the resulting information can be interfaced to control systems and/or displayed. This data aggregation and interpretation provides for fewer false alarms and centralized information display.

Software is provided that allows each node (for example, the nodes 10 or 20 in FIG. 1) to communicate appropriate information back to a central location (for example, the nodes 30 or 50 in FIG. 1). This data can include alarm information and raw data for use in further computations in the central location. The full data transmission can be event driven (e.g. only sent when an event is detected) to minimize band width and reduce complexity. The aggregated data is utilized by the system level data interpretation software as described below. Furthermore, as would be recognized by those skilled in the art, the data aggregation could be performed at several tiers. For example, in one tier, all the data from all the sensors in one building or location could be aggregated (for example at node 30) while sensor data from multiple buildings could be aggregated at a second tier (for example, in a central location 50 as shown in FIG. 1).

In certain embodiment, the present invention proposes extensive software control for both low level and high-level control of node function, code to aggregate and interpret sensor data at a single node, and software to provide for calibration of devices at the point of manufacture and in the field. The array based sensing technology discussed herein uses a pattern matching approach to detect and identify compounds from a library. This library can reside either on the device or at a remote location. Applicant's U.S. Pat. No. 6,422,061 provides additional details of detecting and transmitting sensory data and identification libraries over a network, the disclosure of which is incorporated by reference herein for all purposes. This approach allows for rapid upgrading of instruments as new threats become important. Analysis of live agent test data has indicated a 5-10 (or greater) fold improvement in sensitivity and accuracy is achievable through software optimization at the node.

A network of autonomous sensors reporting to a central location offers the potential to further reduce false alarms and improve alarm prediction through software deployed at the network level. In certain embodiments, the present invention provides an extensive software capability for sensor data fusion. In one embodiment, one module of this system is a symbolic data model that reads discrete data (e.g. alarms, settings) and applies two different mathematical or analytical approaches to identify anomalies. In the first case, a set of rules is applied to this data to generate derived states and anomalies. While the mathematical analysis software is generic, the set of rules must be determined for a given application so the it may best be described as a "knowledge-based" component. In other words, this portion operates on rules such as: if alarm A sounds do nothing unless alarm B sounds. In addition to this rules based module, a second module uses more advanced mathematical tools to identify anomalies. This module utilizes Hidden Markov Models (HMM) to identify anomalies based on probabilities of passing from one state to a second state. The HMM use different algorithms to define these probabilities such as a Viterbi algorithm, a forward-backward algorithm, or a Baum-Welsh algorithm, as would be known to those skilled in the art. All of these methods are designed to find hidden patterns in data. The output is a prediction of an anomaly based on a number of discrete state variables.

Figure 12:
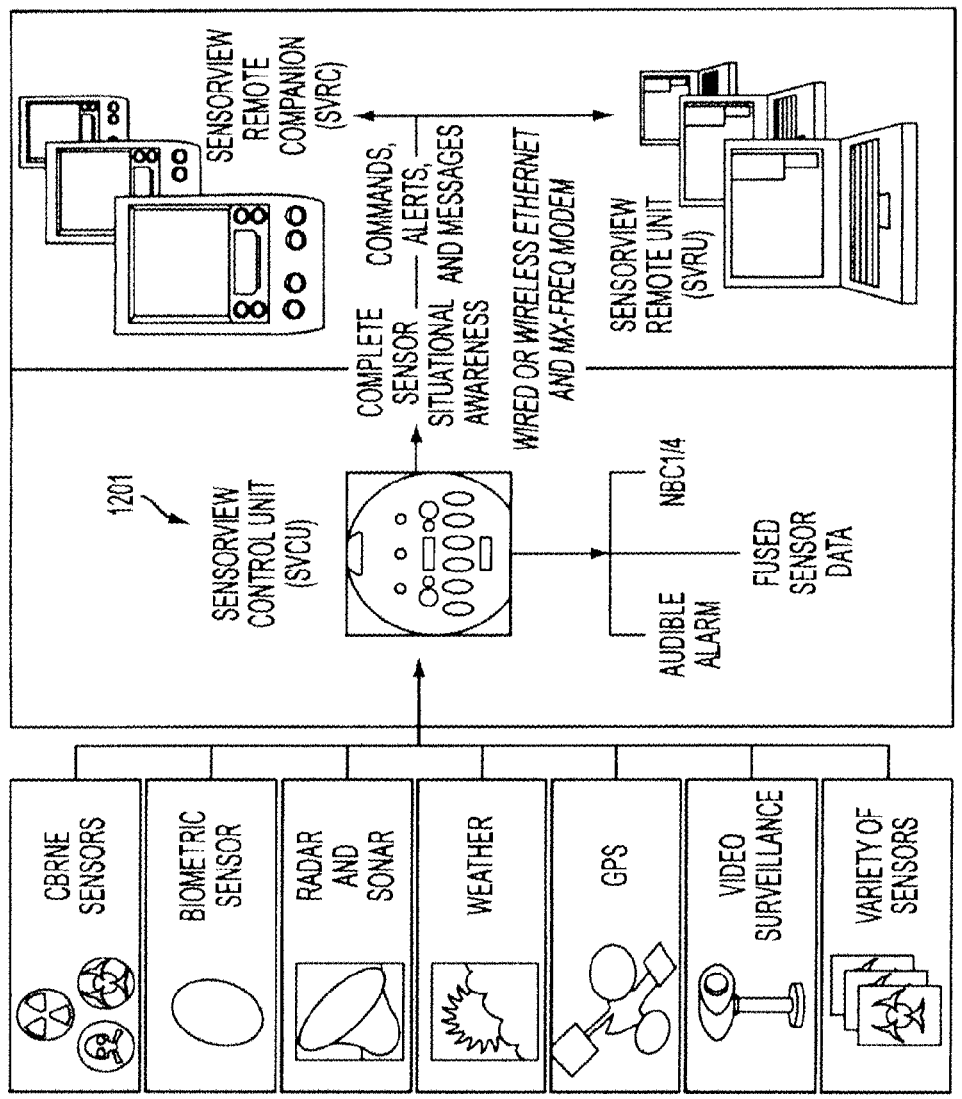
FIG. 12 is a diagram illustrating a graphical user interface that may be displayed at a control station.

An element of the system provides how information is presented. In one embodiment, the system of the present invention is an autonomous system that interfaces with existing control functions by providing a data feed to these existing control systems. In certain other embodiments, the present invention includes other visualization capability such an indication of overall system health with drill down capabilities. In this approach, a central display will present a red light/green light indication (or other similar indicator) of system health/alarm status. On alarm (or system error), further information will be available in graphical form to indicate the fault/alarm location. This capability may prove extremely helpful to first responders or other emergency personnel. An example of such a GUI 1201 that may be used is shown in FIG. 12.

An element of the system is an understanding of node density and distribution throughout the facility both from the perspective of deploying the nodes and interpreting the results received from the nodes. From the perspective of deploying the nodes in a cost and result effective manner, the main principle is that analysis of data from diverse networked sensors generates a system whose performance is significantly better than the sum of its parts. One of the main results of applying this principle is the suppression of false alarms from inexpensive generic sensors. This is achieved by using cutting edge data analysis with a clustered array of networked sensors (whether of the first type sensors and/or second type sensors). At both the array and cluster levels, diverse sensors and optional supplementary sensors such as meteorological ("met"), GPS, may be used. This allows modeling to design clustered array configurations to answer a variety of questions, including: whether supplementary sensor are needed with each sensor, or only with each cluster; what is the optimal distance between sensors and clusters; and what is the effect of weather on specific sensors. The modeling is also used to answer system-level cross-correlation questions such as: what is the best number of sensors per cluster; what is the best mix of sensor types in a cluster; or is there a combination of generic sensors that can cover for each other's failings, with at least one type that works in most relevant weather conditions. The data fusion and analysis approach also provides software that can learn patterns of system behavior and optimize its performance at each particular site. It learns from its mistakes and evolves to become better using techniques such as neural networks which are within the abilities of one skilled in the art.

From the perspective of interpreting results received from particular nodes, certain embodiments of the present invention model different deployment options and node placements and factor that information in the analysis of the data received from the nodes. Therefore, in certain embodiments, the analysis models may give different weightage to different nodes (or sensor arrays) based on the location, type, and or density of nodes in a monitored area. For example, if an area has a large number of first type sensor nodes, a single node indicating the presence of a particular agent when the other nodes do not indicate the presence of such an agent is given less weightage than if the node indicating the agent was in an area with relatively sparse coverage of nodes.

In certain embodiments, the second type sensors (or more sensitive sensors) may be provided with preconcentrators. Such preconcentrators are used for improved performance with analytical equipment such as gas chromatographs and mass spectrometers. More recently, miniaturized versions of these devices have been developed for use with hand held devices. While such a device does offer the possibility of sensitivity and perhaps even specificity enhancements, it does come with a price of additional power needs, reduced system robustness, increased operational costs, and more complex manufacturing. Therefore, this capability may not be used on all nodes and a tradeoff of incorporation of the preconcentrator is made before deciding how many of the nodes would include a preconcentrator.

Figure 13:
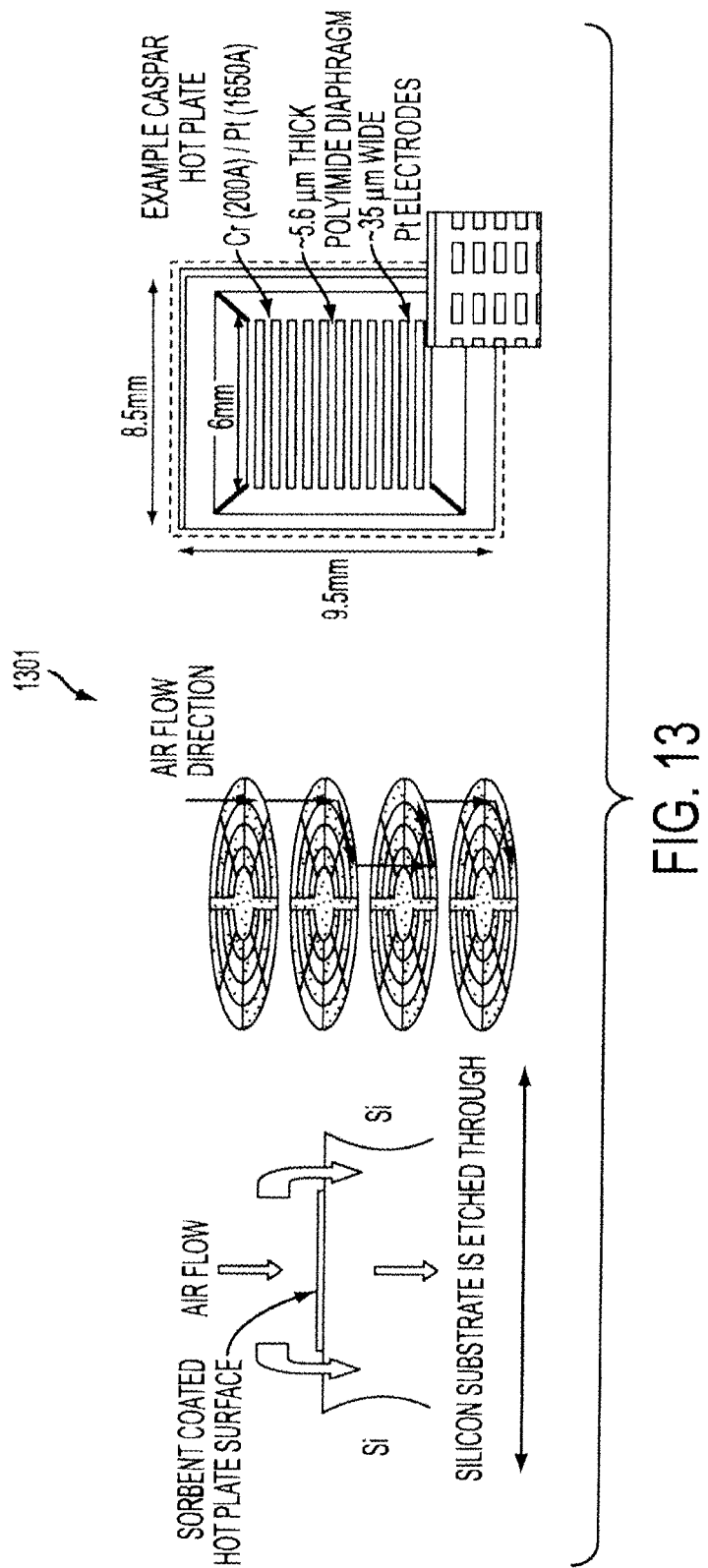
FIG. 13 shows a micromachined preconcentrator.

FIG. 13 shows a micromachined preconcentrator CASPAR 1301 (Cascade Avalanche Sorbent Plate ARray), which can be used to selectively trap analyte(s) of interest and thermally desorb a narrow time width pulse of concentrated analyte into a narrow orifice intake. The design of CASPAR provides a high surface area "collection plate" with an extremely low-pressure drop, to allow a high flow to be passed through the device and intimately contact the majority of the collection surface, with the minimum power expended. Collection flow is directed normal and directly through the surface of CASPAR, which is machined with a dense array of holes or perforations. Approximately 50% of the surface corresponds to air openings. One or more collection plates can be used as necessary. Multiple plates can also be stacked to provide increased collection efficiency, however a single collection plate has been demonstrated as an efficient analyte collector design for explosives and a nerve agent simulant (DMMP).

Alternative micromachined preconcentrator technologies have been developed in which air collection flows are directed parallel to the collection surface. This approach does not allow high airflows, with intimate air to collector surface contact.

The surface of CASPAR is coated with one or more areas of sorbent polymer(s), which act to selectively collect and concentrate analyte at ambient temperatures. The sorbent polymers for a number of analytes including chemical agents have been designed for trapping chemical agents. These materials have also been specifically designed with high temperature stabilities, necessary for thermal cycling. Naval Research Laboratories (NRL) "HC" polymer coated CASPAR devices have been demonstrated to provide very high collection efficiencies for the nerve agent, dimethylmethylphosphonate (DMMP). Even with an "early" non-optimized prototype device, sensitivity gains observed were in the region of multiple orders of magnitude. After thousands of thermal desorption cycles, no degradation in device performance has been observed. Multiple areas of CASPAR coated with different sorbent materials, targeting different agents and TICS, can be thermally desorbed in sequence and from initially different operating temperatures to different desorbing temperatures to provide additional measures of analyte selectivity.

Figure 14:
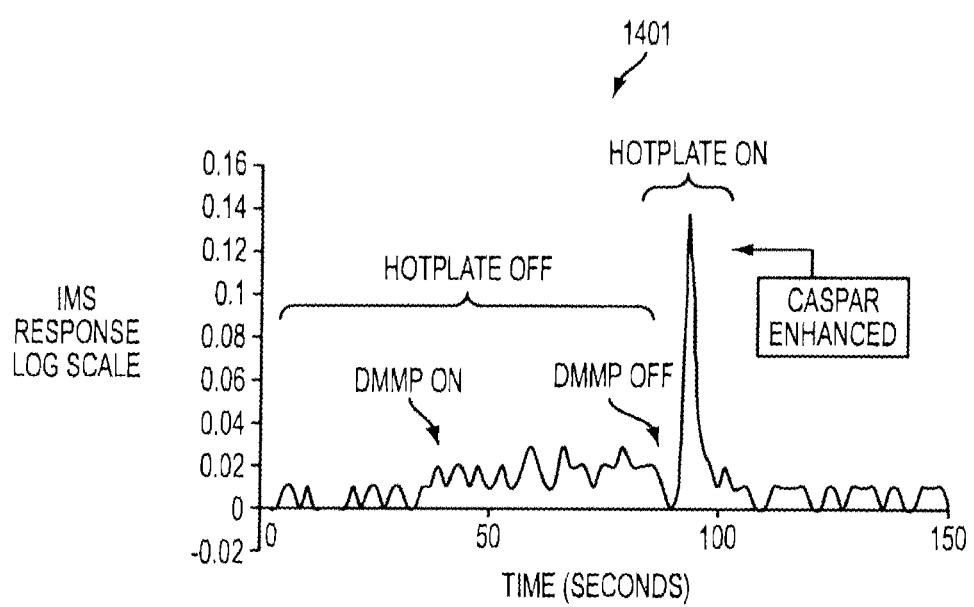
FIG. 14 is graph that illustrates the variation in response of the CASPAR preconcentrator with temperature.

The low thermal mass of CASPAR allows the device to be heated from ambient to analyte desorption temperatures in the milliseconds time domain. This allows the injection of a high concentration analyte sample into the sensor module. CASPAR can be thermally ramped to intermediary temperatures to allow desorption of analytes that correspond to different vapor pressures as shown in the diagram 1401 in FIG. 14. This process offers separation between more volatile analytes such as hydrocarbon fuels, other solvents and analytes of interest such as the chemical agents. In addition, multiple areas of CASPAR coated with different sorbent polymers, targeting different analytes, can be thermally desorbed in sequence to provide additional measures of analyte selectivity. Flow through CASPAR will be provided by a miniature fan during collection and a miniature pump during desorption.

Some of the technology discussed herein are described in greater detail in the following U.S. patents, whose entire disclosures are incorporated herein in their entireties:

U.S. Pat. No. 6,234,006 Hand held sensing apparatus
U.S. Pat. No. 6,085,576 Hand held sensing apparatus
U.S. Pat. No. 6,418,783 Hand held sensing apparatus
U.S. Pat. No. 6,537,498 Colloidal particles used in sensing arrays The invention is described herein with reference to accompanying drawings. These drawings illustrate certain details of specific embodiments that implement the systems and methods and programs of the present invention. However, describing the invention with drawings should not be construed as imposing on the invention any limitations that may be present in the drawings. The present invention contemplates methods, systems and program products on any computer readable media for accomplishing its operations. The embodiments of the present invention may be implemented using an existing computer processor, or by a special purpose computer processor incorporated for this or another purpose.

As noted above, embodiments within the scope of the present invention include program products on computer-readable media and carriers for carrying or having computer-executable instructions or data structures stored thereon. Such computer-readable media can be any available media which can be accessed by a general purpose or special purpose computer. By way of example, such computer-readable media can comprise RAM, ROM, EPROM, EEPROM, CD-ROM or other optical disk storage, magnetic disk storage or other magnetic storage devices, or any other medium which can be used to carry or store desired program code in the form of computer-executable instructions or data structures and which can be accessed by a general purpose or special purpose computer. When information is transferred or provided over a network or another communications connection (either hardwired, wireless, or a combination of hardwired or wireless) to a computer, the computer properly views the connection as a computer-readable medium. Thus, any such a connection is properly termed a computer-readable medium. Combinations of the above should also be included within the scope of computer-readable media. Computer-executable instructions comprise, for example, instructions and data which cause a general purpose computer, special purpose computer, or special purpose processing device to perform a certain function or group of functions.

The invention has been described in the general context of method steps or system components which may be implemented in one embodiment by a program product including computer-executable instructions, such as program modules, executed by computers in networked environments. Generally, program modules include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represent examples of corresponding acts for implementing the functions described in such steps.

The present invention is suitable for being operated in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet. Those skilled in the art will appreciate that such network computing environments will typically encompass many types of computer system configurations, including personal computers, hand-held devices, multi-processor systems, microprocessor-based or programmable consumer electronics, network PCs, minicomputers, mainframe computers, and the like. The invention may also be practiced in distributed computing environments where tasks are performed by local and remote processing devices that are linked (either by hardwired links, wireless links, or by a combination of hardwired or wireless links) through a communications network. In a distributed computing environment, program modules may be located in both local and remote memory storage devices.

Other embodiments of the invention will be apparent to those skilled in the art from a consideration of the specification and the practice of the invention disclosed herein. It is intended that the specification be considered as exemplary only, with the true scope and spirit of the invention also being indicated by the following claims and equivalents thereof.

What is claimed is:

1. A system for monitoring a facility for a plurality of agents, comprising:
    a plurality of agent detection sensor arrays, each of the plurality of agent detection sensor arrays comprising a first agent detection sensor and a second agent detection sensor, the first agent detection sensor being operable to detect a presence of a first agent of the plurality of agents, and the second agent detection sensor being operable to detect the presence of a second agent of the plurality of agents;
    an environmental sensor configured to monitor an environmental condition within the facility; and
    a central analysis unit configured to communicate with the plurality of agent detection sensor arrays and the environmental sensor in a network, the central data analysis unit operable to at least partially configure operation of one or more of the plurality of agent detection sensors in response to the monitored environmental condition.

2. The system as recited in claim 1, wherein the environmental sensor comprises a meteorological sensor, and the monitored environmental condition comprises at least one of humidity, pressure, or temperature within the facility.

3. The system as recited in claim 1, wherein the environmental sensor comprises a global positioning system (GPS) receiver, and the monitored environmental condition comprises a location of an agent detection sensor.

4. The system as recited in claim 3, wherein at least one of the plurality of agent detection sensor arrays is a part of a hand-held device.

5. The system as recited in claim 1, wherein the plurality of agent detection sensor arrays includes a sensor array configured to detect an airborne agent.

6. The system as recited in claim 1, wherein the central analysis unit is configured to communicate in the network with the plurality of agent detection sensor arrays to receive alarm data from one or more of the agent detection sensor arrays when the one or more agent detection sensor arrays detect the presence of an agent, and wherein the central analysis unit is configured to communicate alarm data received from the plurality of agent detection sensor arrays to a central location.

7. The system as recited in claim 1, wherein the facility comprises a building.

8. The system as recited in claim 1, wherein the second level of sensitivity is at least approximately 10 to at least approximately 100 times greater than the first level of sensitivity.

9. A system for monitoring a facility for a plurality of agents, comprising:
    a plurality of agent detection sensor arrays, each of the plurality of agent detection sensor arrays comprising a first agent detection sensor and a second agent detection sensor, the first agent detection sensor and the second agent detection sensor being configured to provide orthogonal detection of the plurality of agents, the first agent detection sensor being operable to detect a presence of a first agent of the plurality of agents, and the second agent detection sensor being operable to detect the presence of a second agent of the plurality of agents; and
    a central analysis unit configured to communicate in a network with the plurality of agent detection sensor arrays to receive alarm data indicating the detection of an agent within the facility, the central analysis unit operable to communicate alarm data to a central location.

10. The system as recited in claim 9, further comprising an environmental sensor, the at least one environmental sensor operable to monitor an environmental condition within the facility.

11. The system as recited in claim 10, wherein the environmental sensor comprises a meteorological sensor, and the monitored environmental characteristic comprises at least one of humidity, pressure, or temperature within the facility.

12. The system as recited in claim 9, wherein the plurality of agent detection sensor arrays includes a sensor array configured to detect an airborne agent.

13. The system as recited in claim 9, wherein the central location is configured to communicate alarm data received from the plurality of agent detection sensor arrays to a hand-held computing system.

14. The system as recited in claim 9, wherein the facility comprises a building.

15. A system for monitoring a facility for one or more agents, comprising:
    a plurality sensors of a first type configured to detect the presence of the one or more agents within the facility, the sensors of the first type having a first level of sensitivity to the one or more agents;
    a plurality of sensors of a second type operable to detect the presence of the one or more agents within the facility, the sensors of the second type having a second level of sensitivity to the one or more agents that is greater than the first level of sensitivity, wherein the number of sensors of the second type is less than the number of sensors of the first type; and a central analysis unit configured to communicate in a network with the plurality of agent detection sensors of the first type and the plurality of agent detection sensors of the second type to monitor the facility for the one or more agents, the central analysis unit configured to initiate operation of at least a selected one of the plurality of sensors of the second type in response to detection of one or more agents by one or more sensors of the first type.

16. The system as recited in claim 15, wherein at least one of the plurality of sensors of the first type is configured to detect one or more agents at an immediately dangerous to life or health level and at least one of the plurality of sensors of the second type is configured to detect the agent at a permissible exposure limit level.

17. The system as recited in claim 15, wherein the central analysis unit is configured to communicate alarm data from the plurality of agent detection sensors to a central location via an other network.

18. The system as recited in claim 17, the central location is configured to communicate alarm data received from the plurality of agent detection sensors to a hand-held computing system via a third network that is different from the network and the other network.

19. The system as recited in claim 15, wherein the facility comprises a building.

\* \* \* \* \*